US010537746B2

(12) United States Patent
Snyder

(10) Patent No.: US 10,537,746 B2
(45) Date of Patent: *Jan. 21, 2020

(54) AUTOMATIC EXTERNAL DEFIBRILLATOR WITH INCREASED CPR ADMINISTRATION TIME

(71) Applicant: KONINKLIJKE PHILIPS N.V., Eindhoven (NL)

(72) Inventor: David Snyder, Bainbridge Island, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

This patent is subject to a terminal disclaimer.

(21) Appl. No.: 15/883,557

(22) Filed: Jan. 30, 2018

(65) Prior Publication Data
US 2018/0161590 A1 Jun. 14, 2018

Related U.S. Application Data

(62) Division of application No. 12/096,756, filed as application No. PCT/IB2006/054707 on Dec. 8, 2006, now Pat. No. 10,124,183.
(Continued)

(51) Int. Cl.
A61N 1/39 (2006.01)

(52) U.S. Cl.
CPC ............ A61N 1/3987 (2013.01); A61N 1/39 (2013.01); A61N 1/39044 (2017.08); A61N 1/3993 (2013.01)

(58) Field of Classification Search
CPC ...................................................... A61N 1/39
See application file for complete search history.

(56) References Cited

U.S. PATENT DOCUMENTS 6,021,349 A   2/2000   Arand et al.
6,041,255 A   3/2000   Kroll
(Continued)

FOREIGN PATENT DOCUMENTS

EP   1588736 A2   10/2005
EP   1595575 A2   11/2005
(Continued)

OTHER PUBLICATIONS

Circulation—Journal of the American Heart Association, "Part 5: Electrical Therapiesautomated External Defibrillators, Defibrillation, Cardioversion, and Pacing"; 2005, pp. IV-35-IV-46.
(Continued)

Primary Examiner — William J Levicky

(57) ABSTRACT

An automated external defibrillator (AED) is described which spends an increased proportion of a rescue in a CPR mode. This is accomplished by use of a single shock protocol which causes the AED to spend less time in shock analysis and delivery activities as compared with the typical multiple shock protocol. An AED of the present invention preferably is configured such that the rescue protocol can be modified or changed easily without the need to remove the battery or use specialized hardware or software. Preferably the shock waveform of the single shock is a biphasic waveform delivering at least 150 Joules of energy and more preferably at least 200 Joules of energy.

15 Claims, 7 Drawing Sheets

Related U.S. Application Data

(60) Provisional application No. 60/751,268, filed on Dec. 16, 2005.

(56) References Cited

U.S. PATENT DOCUMENTS

| | | | |
|---|---|---|---|
| 6,351,671 B1 | 2/2002 | Myklebust et al. | |
| 6,356,785 B1 | 3/2002 | Snyder et al. | |
| 6,370,428 B1 | 4/2002 | Snyder et al. | |
| 2003/0088284 A1* | 5/2003 | Daynes | A61N 1/39 607/5 |
| 2004/0143298 A1 | 7/2004 | Nova et al. | |
| 2004/0176807 A1 | 9/2004 | Freeman | |
| 2008/0215103 A1* | 9/2008 | Powers | A61N 1/3987 607/7 |

FOREIGN PATENT DOCUMENTS

| | | |
|---|---|---|
| WO | 9924114 A | 5/1999 |
| WO | 02072197 A2 | 9/2002 |
| WO | 2004054656 A1 | 7/2004 |
| WO | 2006136975 A2 | 12/2006 |

OTHER PUBLICATIONS

Josephson et al: "The Case for Escalating Protocol and Energy Reserve in External Biphasic Defibrillators"; Medtronic Physio-Control, 2001, 4 Page Document.

Stickney: "Treatment of Refibrillation: Continue the Minute of CPR or Immediately Defibrillate"; Medtronic Physio-Control, 2000 4 Page Document.

"Heartstart Home Defibrillator-HS1" Manual, 4th Ed., Nov. 2002, PUBL.#M5068A-91900, Philips Electronics North America Corp.

Heartstream Forrunner Manual, 1997, Hearstream, Inc., USA.

"Heartstart FR2 Defibrillator", 10th Ed, Sep. 2002, Publ. #M3840-91900, Koninklijke Philips Electronics K.V.

Hazinski et al: "Major Changes in the 2005 AHA Guidelines for CPR and ECC:Reaching the Tipping Point for Change"; Circulation, 2005, pp. IV-206-IV-211.

Nolan et al: "European Resuscitation Council Guidelines for Resuscitation 2005: Section 4. Adult Advanced Life Support"; Resuscitation (2005), 67S1, pp. S39-S86.

* cited by examiner

AUTOMATIC EXTERNAL DEFIBRILLATOR WITH INCREASED CPR ADMINISTRATION TIME

This application is a divisional application of U.S. patent application Ser. No. 12/096,756 filed on Jun. 9, 2008, which is a U.S. National Stage Entry of International Patent Application No. PCT/IB2006/054707 filed on Dec. 8, 2006, which in turn claims priority from U.S. Provisional Patent Application No. 60/751,268 filed on Dec. 16, 2005.

The invention relates generally to electrotherapy circuits, and more particularly, to automatic external defibrillators which provide for increased proportions of time for the administration of CPR relative to time spent in the administration of defibrillation.

Automatic external defibrillators ("AEDs") deliver a high-voltage impulse to the heart in order to restore normal rhythm and contractile function in patients who are experiencing arrhythmia, such as ventricular fibrillation ("VF") or ventricular tachycardia ("VT") that is not accompanied by a palpable pulse. There are several classes of defibrillators, including manual defibrillators, implantable defibrillators, and automatic external defibrillators. AEDs differ from manual defibrillators in that AEDs they are pre-programmed to automatically analyze the electrocardiogram ("ECG") rhythm to determine if defibrillation is necessary and to provide administration measures such as shock sequences and CPR periods. There is no need, and in most cases no ability, for a rescuer to be concerned with setup of the rescue protocol. This differs from manual defibrillator which are used by expert medical professionals skilled at setting up all of the defibrillation parameters needed for a particular rescue.

FIG. 1 is an illustration of an AED 10 being applied by a user 12 to resuscitate a patient 14 suffering from cardiac arrest. In sudden cardiac arrest, the patient is stricken with a life threatening interruption to the normal heart rhythm, typically in the form of VF or VT that is not accompanied by a palpable pulse (i.e., shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient will die. Conversely, the quicker defibrillation can be applied after the onset of VF, the better the chances that the patient 14 will survive the cardiac event.

In the use of the AED a pair of electrodes 16 are applied across the chest of the patient 14 by the user 12 in order to acquire an ECG signal from the patient's heart. The defibrillator 10 then analyzes the ECG signal for signs of arrhythmia. If a treatable arrhythmia is detected, the defibrillator 10 signals the user 12 that a shock is advised. After detecting VF or other shockable rhythm, the user 12 then presses a shock button on the defibrillator 10 to deliver defibrillation pulse to resuscitate the patient 14.

Recent studies have shown that different patients may be resuscitated more effectively with different treatment regimes depending upon various factors. One factor which affects the likelihood of success of defibrillation is the amount of time that has elapsed since the patient experienced the arrhythmia. This research has indicated that, depending on the duration of cardiac arrest, a patient will have a better probability of recovery with one protocol as compared to another. If the AED is set up for a less effective protocol for the resuscitation of a particular patient, that patient's probability of recovery may be reduced. These studies have shown that some of these patients have a better chance of being resuscitated if CPR is performed first, to start some circulation which may bring the patient to a condition where application of a shock will be successful. There is also evidence that an AED rescue protocol which provides CPR earlier in the cardiac rescue improves the prospects for long-term survivability. Rescue protocols which provide for an uninterruptible CPR period are described in U.S. patent application No. 60/737,187 filed Nov. 16, 2005 and entitled "AED HAVING MANDATORY PAUSE FOR ADMINISTERING CPR." Furthermore, there is evidence that a rescue protocol which maximizes the proportion of CPR time to defibrillation-related activity can improve survivability. Accordingly it is desirable to provide an AED which calls for CPR early during a rescue and increases the ratio of the time allotted for CPR administration relative to the time related to shock administration.

In accordance with the principles of the present invention, an AED is described which provides for an increase in the proportion of CPR time relative to time spent in shock administration activities. The AED is preset prior to a rescue for a rescue protocol which, when a shock is advised, will deliver a single biphasic shock of at least 150 Joules and preferably of 175 Joules or greater. Preferably the single shock protocol is pre-programmed as the default protocol for the AED Following administration of the single biphasic shock the AED goes into a CPR pause period during which CPR may be administered by the rescuer.

In accordance with a further aspect of the present invention the AED may be easily set to the single shock protocol if currently set for a multiple shock protocol. Setting the single shock protocol may be done with the user interface of the AED without removal of the battery.

In accordance with yet another aspect of the present invention the CPR pause period is followed by analysis of the ECG waveform and, if a shock is advised, either a single shock or multiple shock sequence is delivered.

IN THE DRAWINGS

Figure 1:
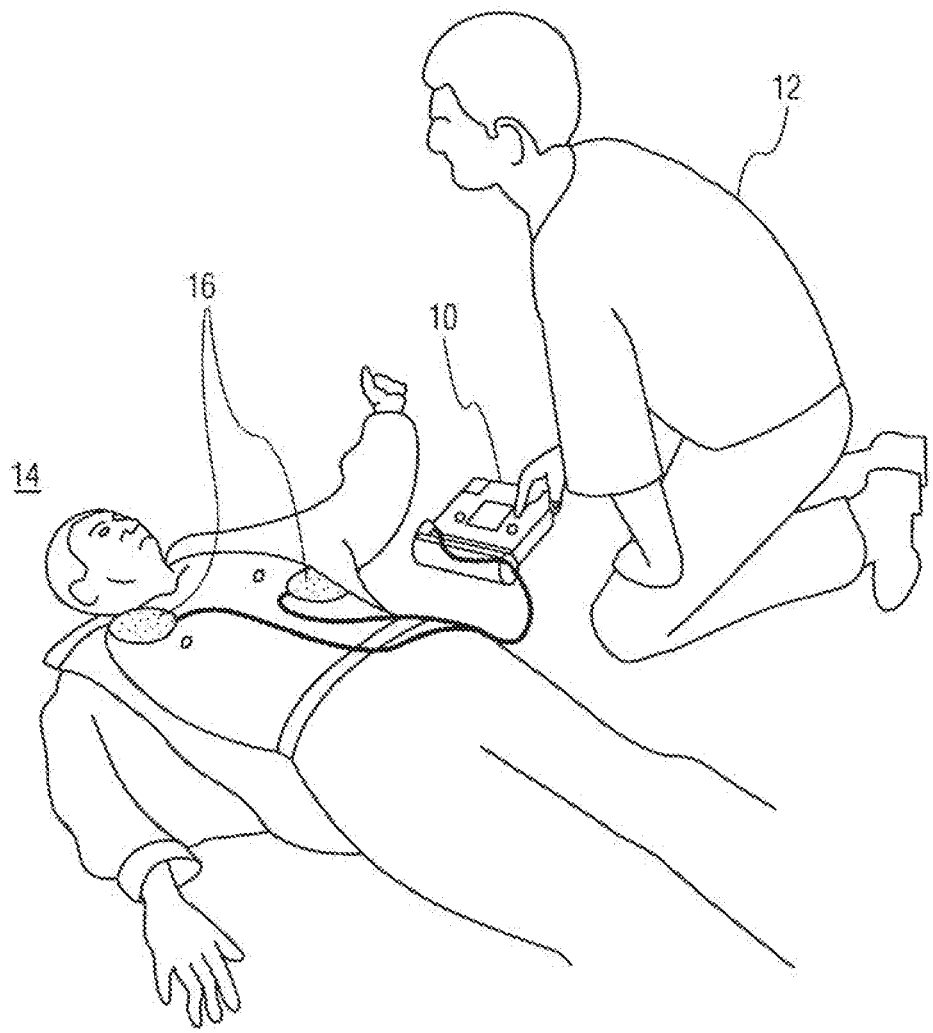
FIG. 1 is an illustration of a defibrillator being applied to a patient suffering from cardiac arrest.
Figure 2:
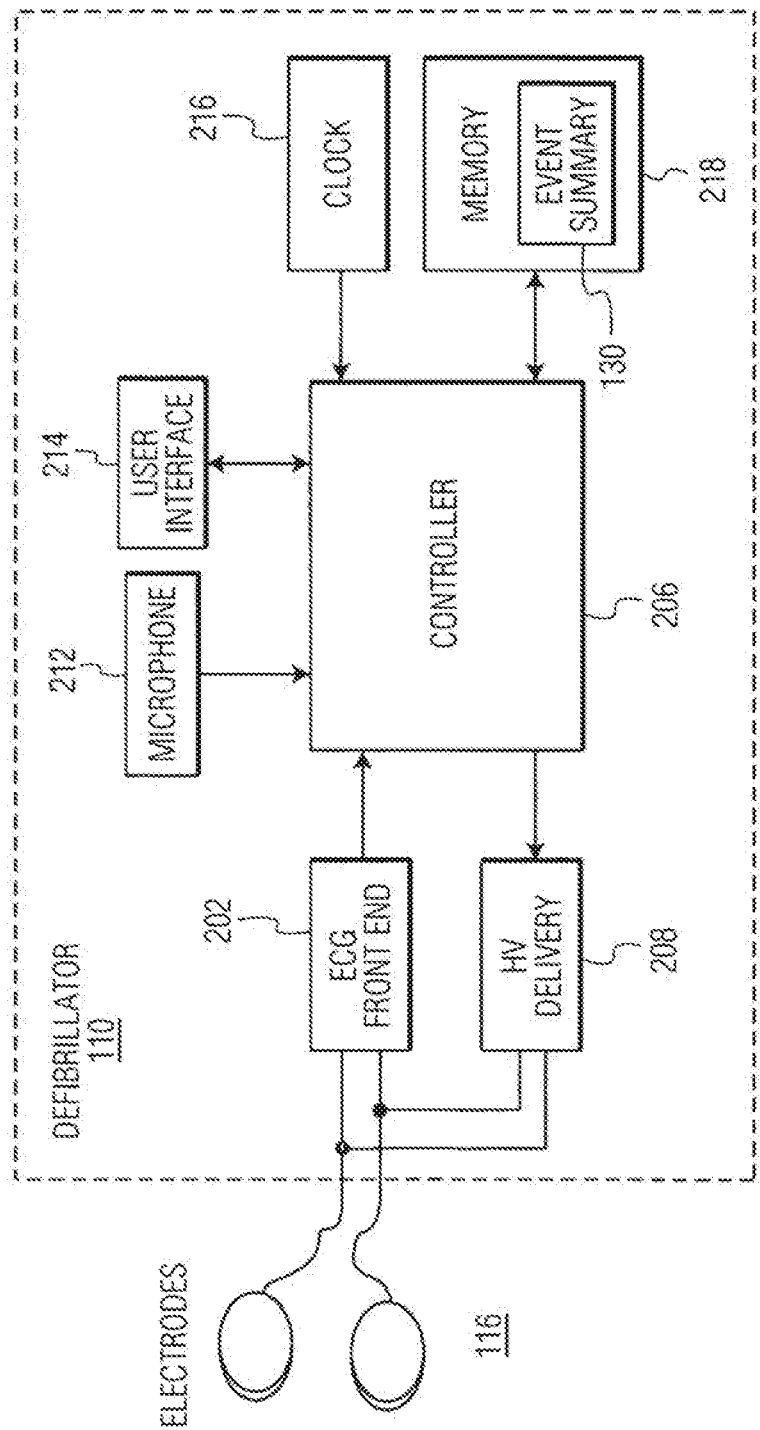
FIG. 2 is a block diagram of a defibrillator constructed in accordance with the principles of the present invention.

FIG. 2 illustrates an AED 110 constructed in accordance with the principles of the present invention. The AED 110 is designed for small physical size, light weight, and relatively simple user interface capable of being operated by personnel without high training levels or who otherwise would use the defibrillator 110 only infrequently. In contrast, a paramedic or clinical (manual) defibrillator of the type generally carried by an emergency medical service (EMS) responder tends to be larger, heavier, and have a more complex user interface capable of supporting a larger number of manual monitoring and analysis functions and protocol settings.

An ECG front end circuit 202 is connected to a pair of electrodes 116 that are connected across the chest of the patient 14. The ECG front end circuit 202 operates to amplify, buffer, filter and digitize an electrical ECG signal generated by the patient's heart to produce a stream of digitized ECG samples. The digitized ECG samples are provided to a controller 206 that performs an analysis to detect VF, shockable VT or other shockable rhythm and, in accordance with the present invention, that performs a treatment regime which provides a relatively high proportion of CPR to the patient. If a shockable rhythm is detected, the controller 206 sends a signal to HV (high voltage) delivery circuit 208 to charge a high voltage capacitor of circuit 208 in preparation for delivering a shock, and a shock button on a user interface 214 is activated to begin flashing. The rescuer is then advised by an audible instruction to keep away from the patient ("hands off" instruction). When the rescuer presses the shock button on the user interface 214 a defibrillation shock is delivered from the HV delivery circuit 208 to the patient 14 through the electrodes 116.

The controller 206 is coupled to further receive input from a microphone 212 to produce a voice strip. The analog audio signal from the microphone 212 is preferably digitized to produce a stream of digitized audio samples which may be stored as part of an event summary 130 in a memory 218. The user interface 214 may consist of a display, an audio speaker, and control buttons such as an on-off button and a shock button for providing user control as well as visual and audible prompts. A user interface of the present invention may also include one or more control buttons for selecting a rescue protocol stored in memory 218 to be carried out during a rescue. A clock 216 provides real-time or elapsed time clock data to the controller 206 for time-stamping information contained in the event summary 130. The memory 218, implemented either as on-board RAM, a removable memory card, or a combination of different memory technologies, operates to store the event summary 130 digitally as it is compiled during the treatment of the patient 14. The event summary 130 may include the streams of digitized ECG, audio samples, and other event data as previously described.

The AED of FIG. 2 has several treatment rescue protocols or treatment modes stored in which may be selected during setup of the AED when it is initially received by the EMS service. One type of protocol is the "shock first" protocol. When the AED is set up for this protocol, the AED will, when connected to a patient and activated, immediately analyze the patient's ECG heart rhythm to make a heart rhythm classification. If the analysis determines that an arrhythmia treatable with electrical defibrillation is present, typically either ventricular fibrillation (VF) or pulseless ventricular tachycardia (VT), the rescuer is informed and enabled to deliver the shock. If it is determined that the arrhythmia is not treatable with a defibrillation shock, the AED will go into a "pause" mode during which CPR may be performed.

The second type of protocol is the "CPR first" protocol. When the AED is set up for this protocol, the AED will begin operating by instructing the rescuer to administer CPR to the patient. After CPR is administered for a prescribed period of time, the AED begins to analyze the ECG data to see if an arrhythmia treatable with electrical defibrillation is present.

In accordance with the principles of the present invention the AED 110 has the ability to execute either a multiple shock or single shock protocol, the latter providing one or more periods for CPR which are a greater proportion of the time of the rescue in relation to the time spent by the AED in defibrillation shock-related activities, as described in detail below. Preferably the single shock protocol is the default protocol, that is, the AED is preset for a single shock protocol at the time it is received by the EMS service. The AED can be set to the default setting at the factory or by a service person before it is put into use by the EMS service. Thus, when the AED is received by the EMS service it is ready for service immediately with the single shock protocol after installation of the battery and the automatic execution of a self-test, with no further setup required. If the EMS service prefers a multiple shock protocol the protocol setting can be changed by a service person or by an AED administrator or other authorized individual of the EMS service to the desired protocol, as described below. Preferably the protocol setting can be changed using the controls of the user interface 214, and without undue manipulation complexity such as use of special hardware or software. It is preferable that the protocol setting be changeable without the need to power down the AED.

In accordance with a further aspect of the present invention the single shock protocol of the AED of FIG. 2 delivers a single biphasic shock waveform rather than a monophasic pulse. The energy level delivered by the single biphasic shock is at least as high as the energy level of a shock of the AED's multiple shock sequence. An energy level in excess of 150 Joules is desirable with an energy level in excess of 175 Joules being preferable and an energy level in excess of 200 Joules being more preferable. (Actual delivered energies may differ somewhat from the intended dose delivery as a function of patient impedance.) In general, the single biphasic shock will usually be at or greater than the energy level of the highest energy shock level of a multiple shock sequence.

Figure 3:
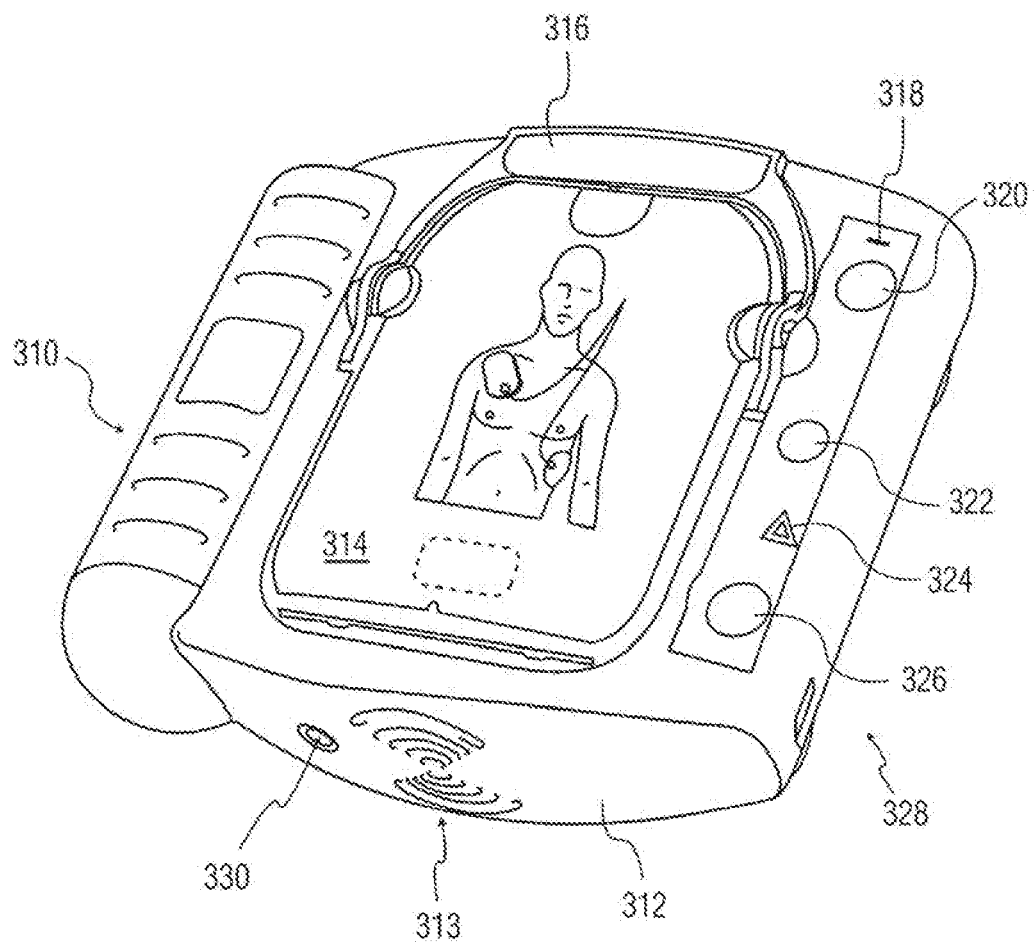
FIG. 3 illustrates an AED with an audible user interface.

Referring now to FIG. 3, an over-the-counter (OTC) AED 310 is shown in a top perspective view. The OTC AED 310 is housed in a rugged polymeric case 312 which protects the electronic circuitry inside the case and also protects the layperson user from shocks. Attached to the case 312 by electrical leads are a pair of electrode pads. In the embodiment of FIG. 3 the electrode pads are in a cartridge 314 located in a recess on the top side of the OTC AED 310. The electrode pads are accessed for use by pulling up on a handle 316 which allows removal of a plastic cover over the electrode pads. The user interface is on the right side of the AED 310. A small ready light 318 informs the user of the readiness of the OTC AED. In this embodiment the ready light blinks after the OTC AED has been properly set up and is ready for use. The ready light is on constantly when the OTC AED is in use, and the ready light is off or flashes in an alerting color when the OTC AED needs attention.

Below the ready light is an on/off button 320. The on/off button is pressed to turn on the OTC AED for use. To turn off the OTC AED a user holds the on/off button down for one second or more. An information button 322 flashes when information is available for the user. The user depresses the information button to access the available information. A caution light 324 blinks when the OTC AED is acquiring heartbeat information from the patient and lights continuously when a shock is advised, alerting the rescuer and others that no one should be touching the patient during these times. Interaction with the patient while the heart signal is being acquired can introduce unwanted artifacts into the detected ECG signal. A shock button 326 is depressed to deliver a shock after the OTC AED informs the rescuer that a shock is advised. An infrared port 328 on the side of the OTC AED is used to transfer data between the OTC AED and a computer. This data port finds used after a patient has been rescued and a physician desires to have the OTC AED event data downloaded to his or her computer for detailed analysis. A speaker 313 provides voice instructions to a rescuer to guide the rescuer through the use of the OTC AED to treat a patient. A beeper 330 is provided which "chirps" when the OTC AED needs attention such as electrode pad replacement or a new battery.

When configured in accordance with the prior art the OTC AED 310 was configured by the factory and shipped to customers with a three-shock default protocol. No instructions were given for a user to change the protocol; if the owner or a potential rescuer desired a single shock or other protocol, the protocol could only be changed by an authorized individual using special setup software. However, when the OTC AED is designed in accordance with the present invention it is configured at the factory for delivery to the customer with a single shock protocol as the default protocol setting. In accordance with a further aspect of the present invention, the protocol can be changed from the user interface of the AED without removal of the battery or other specialized hardware or software. An authorized individual depresses the information button 322 three times or in another specialized sequence. This action causes the speaker 313 to announce that the AED is in the setup mode and the listener is given one or more options including protocol selection. By following the audible instructions the authorized individual is able to change the default single shock protocol to another protocol setting or to modify the single shock protocol as illustrated below.

It will be appreciated that when the AED 310 is intended for layperson use without the assistance of trained EMS personnel, it will still be desirable for adjustment of the protocol setting to be done only by authorized personnel and not by layperson users of the AED.

Figure 4:
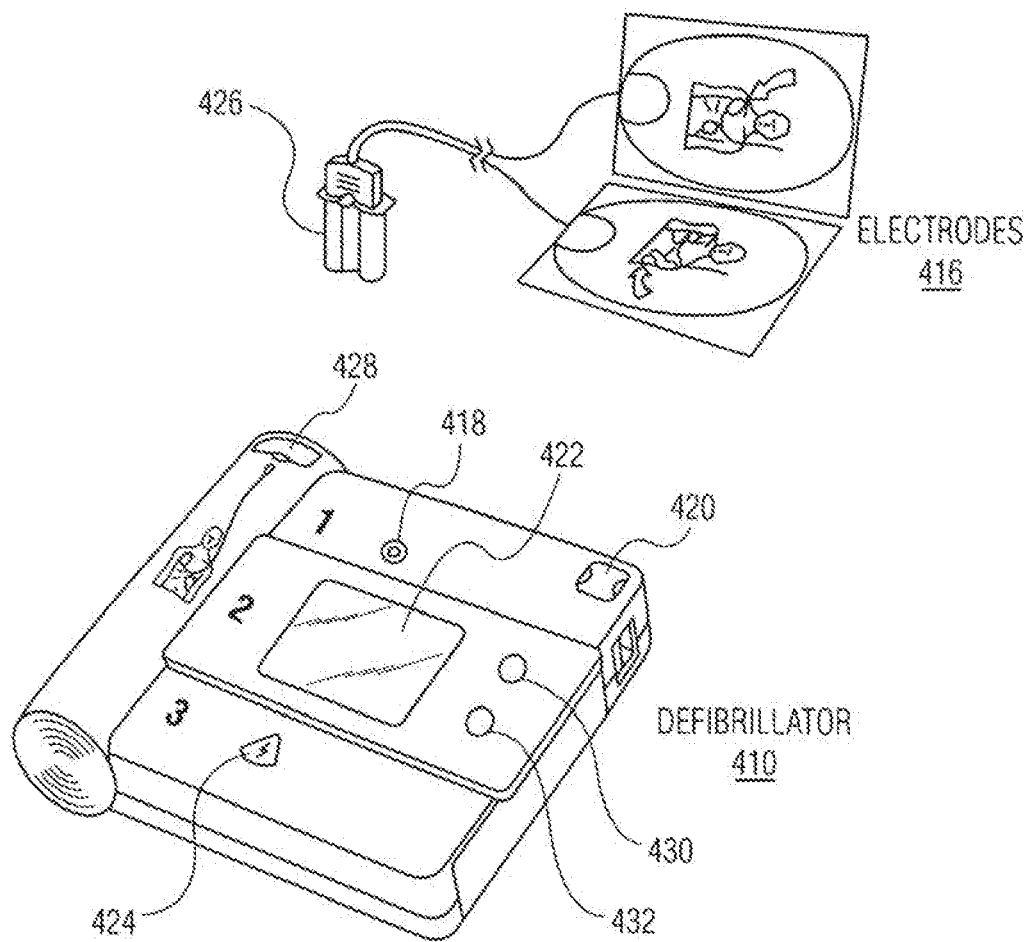
FIG. 4 illustrates an AED with a visual user interface.

FIG. 4 illustrates a defibrillator according to another example of the present invention. This AED 410 has a pair of electrodes 416 with a connector 426 which is designed for insertion into a socket 428 on the AED 410. Located on a top surface of the AED 410 is the user interface, including an on-off switch 418 that activates the AED 410 and begins the process of audibly prompting the user to attach the electrodes 416 to the patient 14. A status indicator 420 provides a continual visual indication of the defibrillator status and the available battery charge. A display 422 provides for display of text such as user prompts and graphics such as ECG waveforms. A shock button 424 provides for delivery of the shock to the patient 14 if ECG analysis indicates that a shockable rhythm is present. Administration of defibrillation shocks is done by prompting the user 12 to manually press the shock button 424.

When configured in accordance with the prior art the AED 410 is provided to a customer with a three-shock protocol as the default protocol. Authorized individuals may change or adjust the treatment protocol to others such as a single shock protocol by several different procedures. One procedure is to remove the battery of the AED and insert a specially configured setup card into the unit. When the battery is reinstalled the AED 410 will power up and show a setup menu on the display 422. The desired protocol changes can be made from the setup menu or by reading setup data from the setup card. During setup the AED cannot be used for defibrillation. At the completion of setup the AED is turned of and the battery is removed again. The setup card is then removed from the AED and the battery is reinstalled. The AED may now be powered up to the new setup configuration.

Another procedure is to remove the battery and install a specialized administration battery pack. While the administration battery pack is being installed the user holds down two option buttons 430 and 432 on the user interface. When the AED 410 is powered up with the administration battery pack installed, setup software is run to display the setup menu on the display 422. At the conclusion of the setup process the AED is powered down, the administration battery pack is removed, the operational battery is reinstalled, and the AED may then be used in its new protocol configuration.

Yet another procedure is to receive new setup data by means of the AED's infrared port 328 (not shown in FIG. 4). The setup data can be received from a transmission by another AED 410 for by transmission from a computer running specialized setup software.

In accordance with the principles of the present invention the AED 410 is configured at the factory for delivery with a single shock protocol as the default protocol. The customer may then use the AED 410 immediately after battery installation and self-test as a single shock AED. Any of the previously discussed procedures may be employed to change the protocol to a multiple shock protocol or adjust the single shock protocol as described below. Alternatively, the single shock protocol may be modified for variation of the CPR period as discussed below and/or the protocol may be changed to a multiple shock protocol from the user interface without removal of the battery or communication with another AED or computer. A special depression of the user interface buttons such as holding down both option buttons 430 and 432 while depressing the shock button 424 or other specialized button sequence enables authorized personnel to bring the setup menu to the display 422 for modification and/or change of the shock treatment protocol.

Figure 5:
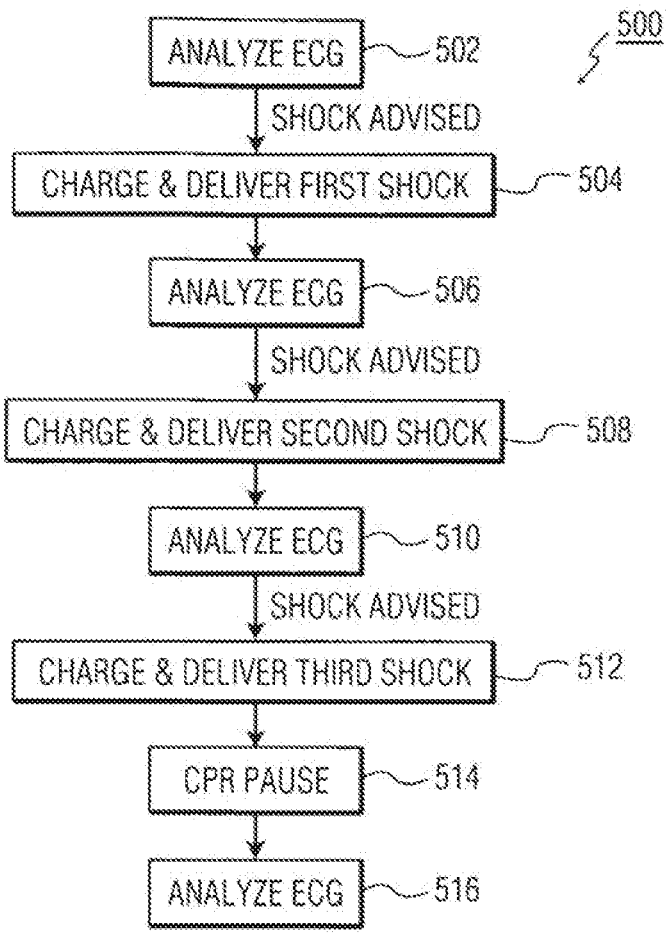
FIG. 5 illustrates a three-shock defibrillation protocol of the prior art.
Figure 6:
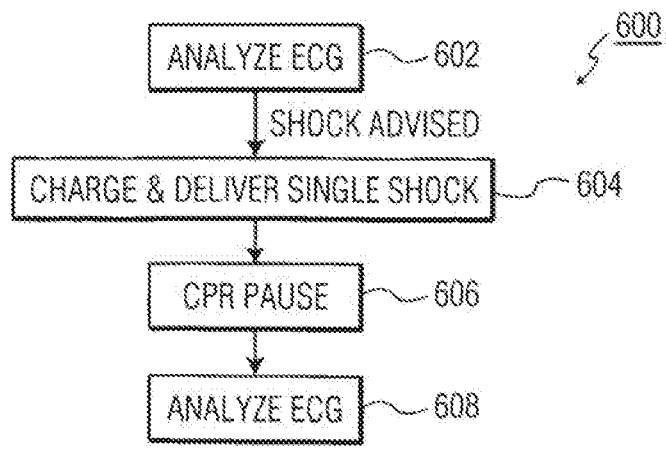
FIG. 6 illustrates a single shock defibrillation rescue protocol of the present invention.

Turning now to FIGS. 5 and 6, an illustration of the increased proportion of time spent in CPR in a rescue protocol of the present invention is seen by a comparison of the two flowcharts. FIG. 5 illustrates a flowchart of a typical three shock treatment protocol 500. At step 502 the AED begins by analyzing the patient's ECG waveform. If a shock is advised (the only outcome in these illustrations), the AED charges its high voltage circuitry and delivers a first shock at step 504. After signal artifacts resulting from shock delivery have sufficiently dissipated the ECG is analyzed again at step 506 to ascertain whether a normal heart rhythm has returned or another shock is required. If it is determined that another shock is advised, the AED charges the high voltage circuitry again and delivers a second shock at 508. After delivery of the second shock the ECG waveform is analyzed again at 510 to see if a normal heart rhythm has returned or a further shock is required. If a shock is advised the AED charges and delivers a third shock at 512. Following the third shock in this example the AED begins a CPR pause period 514, during which time the rescuer may receive audible instructions in the administration of CPR. At the conclusion of the CPR pause period the ECG is analyzed to determine whether another shock sequence is advised. It can be seen that the three shock sequence of operation spends a considerable amount of time analyzing and preparing for electrotherapy as compared to the time dedicated to CPR.

In comparison FIG. 6 illustrates a typical single shock sequence 600 of the present invention. As in the sequence of FIG. 5, this protocol begins at 602 with the AED analyzing the ECG waveform to see whether a shock is advised. When a shock is advised the AED charges the high voltage circuitry at 604 and delivers a single biphasic shock. As mentioned previously, the single shock will deliver energy at the level of the greatest level delivered by a shock of the three shock sequence, preferably at a level of 175 Joules or greater and more preferably at a level of 200 Joules or greater. After delivery of the single shock the AED in this example goes into a CPR pause period at 606, during which CPR is administered. At the end of the CPR period the AED analyzes the ECG waveform at 608 to determine whether a normal heart rhythm has returned or another shock is required. ECG analysis may start during the CPR pause period if artifacts of chest compression are sufficiently filtered from the processed data. It is seen that a significantly greater proportion of time is spent in CPR delivery during the single shock sequence 600 as compared to the three shock sequence 500 of FIG. 5.

Figure 7:
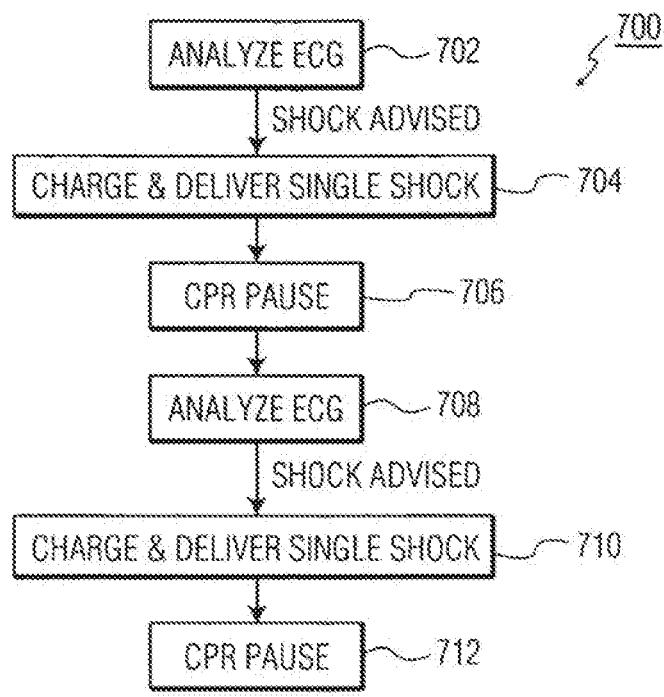
FIG. 7 illustrates a second single shock defibrillation protocol of the present invention.

FIG. 7 illustrates a second single shock protocol 700 of the present invention. The protocol 700 begins with ECG analysis at 702, charge and delivery of a single shock at 704 when a shock is advised, and a CPR pause period at 706 followed by another analysis of the ECG waveform at 708, all as previously discussed in FIG. 6. If a normal heart rhythm has not returned and another shock is advised, the AED charges and delivers another single biphasic shock at 710. Following this second shock delivery the AED enters another CPR pause period. It is seen in this example that every delivery of a defibrillation shock is followed by a period of CPR administration to provide a significant amount of CPR treatment to the patient. Since the circulation promoted by CPR can increase the prospect for a successful defibrillation, this protocol can often result in a successful rescue, particularly for patients with significant downtime prior to rescue.

Figure 8:
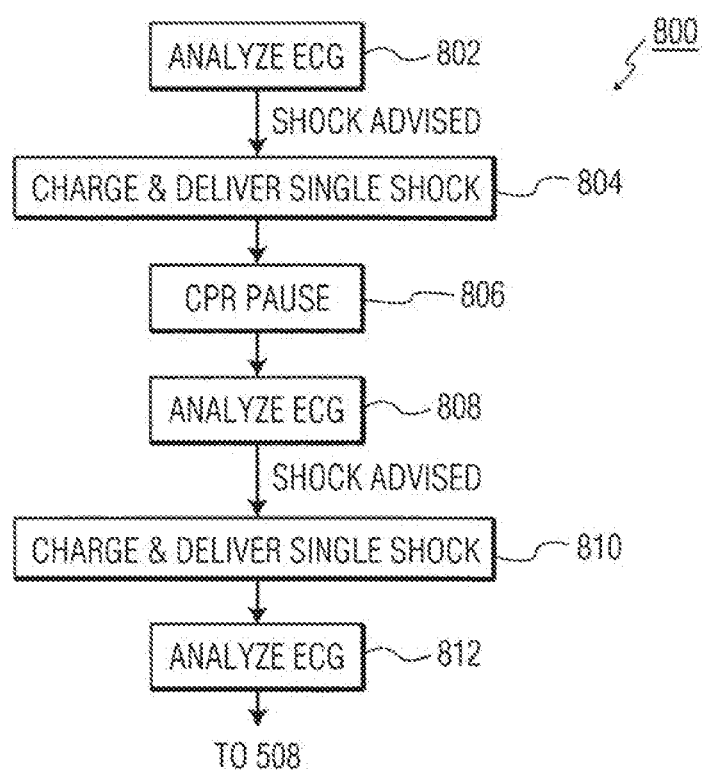
FIG. 8 illustrates a single and multiple shock defibrillation protocol of the present invention.

FIG. 8 illustrates a rescue protocol 800 of the present invention which utilizes both a single shock and multiple shock sequences. This sequence begins with the same four steps 802-808 as discussed previously. When a shock is advised after analysis of the ECG waveform at 808 the protocol begins a three shock sequence by charging the high voltage circuitry and delivering the first shock of the three shock sequence at 810. After delivery of this first shock of three, the AED analyzes the ECG waveform to determine whether a normal heart rhythm has returned or a further shock is advised. If a shock is advised the sequence continues with steps 508-512 as discussed above before pausing for another CPR pause period. The patient thus receives the benefits of both a single shock and a multiple shock sequence with this protocol.

FIG. 8 illustrates another protocol 900 of the present invention which begins immediately at 902 with administration of CPR. During or at the end of the CPR pause period the AED analyzes the ECG waveform at 904. If a shock is advised the AED charges and delivers a single biphasic shock at 906, followed by another CPR pause period at 908. Treatment continues with steps 708 or 808 and their following steps for a single shock or mixed shock sequence, respectively. It is seen that the protocol 900 provides the greatest percentage of time for CPR of the illustrated exemplary protocols.

Figure 9:
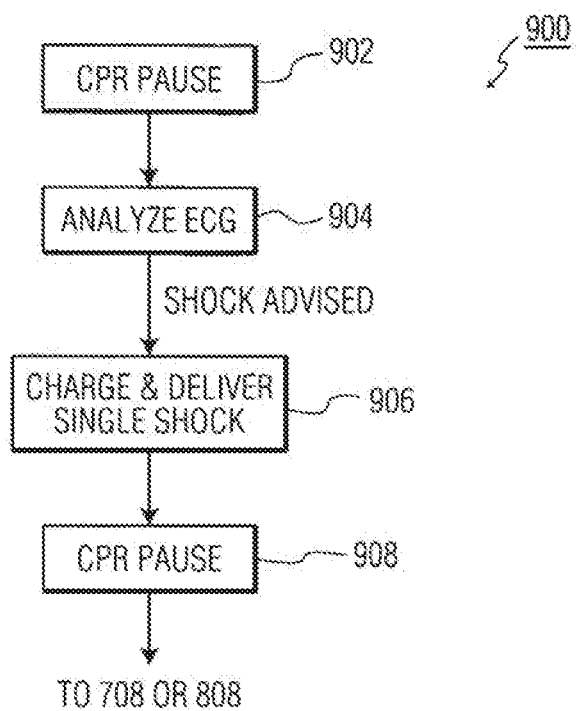
FIG. 9 illustrates a third single shock defibrillation protocol of the present invention.

The AED 110 of FIG. 2 has a further option, which is to recommend a treatment protocol, such as a shock first (e.g., FIG. 6) or CPR first (e.g., FIG. 9) protocol, as discussed more fully in concurrently filed U.S. patent application Ser. No. 11/917,212 entitled "DEFIBRILLATOR WITH AUTOMATIC SHOCK FIRST/CPR FIRST ALGORITHM." This is done by the AED which begins by analyzing the patient's ECG waveform and calculating and evaluating a return of spontaneous circulation (ROSC) score as described below. From the evaluation of the ROSC score a treatment protocol is recommended. The recommended protocol may be immediately carried out by the AED, or the recommendation presented to the rescuer for his or her final decision on the treatment protocol to be carried out.

Figure 10:
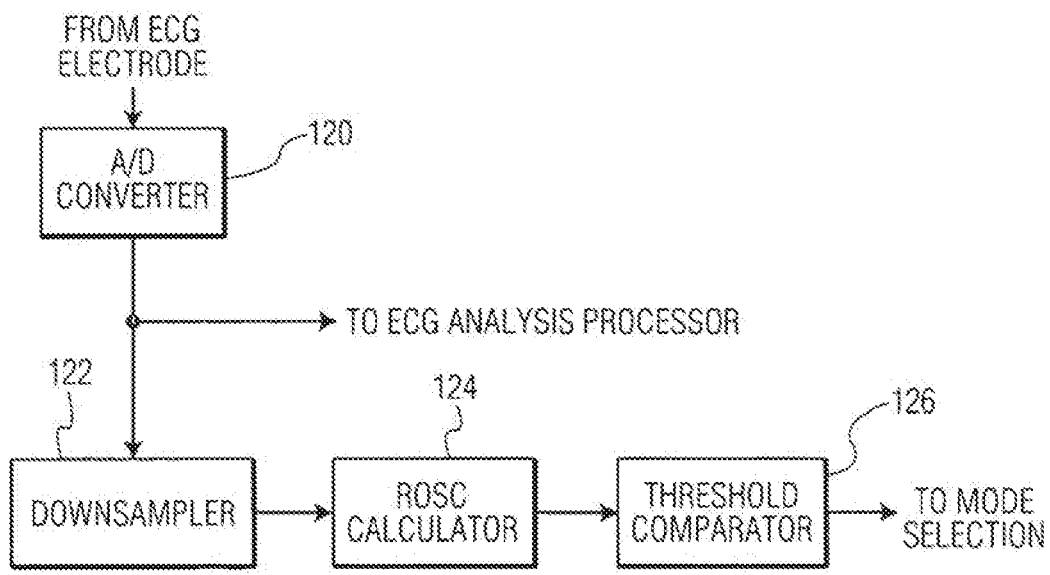
FIG. 10 is a detailed block diagram of a resuscitation predictor suitable for use with a resuscitation protocol of the present invention.

FIG. 10 illustrates a portion of the ECG front end circuit 202 and controller 206 of FIG. 2 which operate to recommend a treatment protocol which is likely to be effective for the patient. As previously mentioned the electrodes 116 provide ECG signals from the patient which are sampled (digitized) by an A/D converter 20. The digitized ECG signals are coupled to the ECG analysis processor in the controller which analyzes the ECG waveform to determine whether application of a shock is advised. The ECG samples are coupled to a downsampler 22 which subsamples the stream of ECG samples to a lower data rate. For instance, a data stream of 200 samples/sec may be downsampled to 100 samples/sec. The downsampled ECG data is coupled to a ROSC calculator 24 which determines a sequence of ROSC scores from the ECG data. The ROSC scores are compared against a threshold by threshold comparator 26 to determine a mode of treatment which is most likely to lead to a successful resuscitation. This mode determination is coupled to the mode selection portion of the controller, which either selects the desired mode automatically or presents the mode as a recommendation to the rescuer who may then either decide to follow the recommended mode or an alternate treatment regime.

The ROSC calculator 24 may be operated in several ways. For one example, the ROSC score can be calculated as the mean magnitude of the bandwidth limited first derivative (or first difference, which is a discrete-time analog) of the ECG over a period of a few seconds. Since the bandwidth limited first derivative may already be calculated for arrhythmia detection by the controller 206, the additional computation may involve only the additional calculation of an average. This process can be implemented as a real-time measure by means of a moving average requiring only one addition and one subtraction per sample. For instance, the difference of successive samples may be taken for a stream of samples received over a period of 4.5 seconds at a 100 sample/sec rate. The signs of the differences are discarded to produce absolute values, which are summed over the 4.5 second interval. This produces a ROSC score value which is equivalent to a frequency weighted average amplitude of the ECG waveform. The score may be scaled or further processed in accordance with the architecture and demands of the instant system.

Since the spectrum of the first derivative is proportional to frequency, the ROSC score is largely unaffected by CPR artifact, most of which will be very low frequency.

Another alternative way to calculate a mean value is to square the differences of the consecutive samples, then sum the products and take the square root of the sum. This produces an RMS (root mean square) form of ROSC score.

As an alternative to the mean value computation, another approach is to use the median magnitude of the first derivative. This approach is more computationally intensive, but can advantageously be more robust to noise. Care must be taken to avoid de-emphasizing the signal that gives the measure its discriminating power. In another embodiment, a trimmed mean or min-max calculation can offer a favorable compromise. By eliminating the largest outliers, greater immunity to impulse artifacts (e.g. physical disturbances of the electrode pads) can be provided. By eliminating the largest outliers, the occasional high amplitude artifact which would occur relatively infrequently can be eliminated without significantly reducing the discriminating power associated with the data of cardiac origin.

What is claimed is:

1. An automatic external defibrillator (AED) comprising:
a pair of electrode pads;
an ECG processor coupled to the electrode pads and operable to analyze ECG signals to determine whether a shock is advised;
a high voltage circuit coupled to the electrode pads for the delivery of a biphasic defibrillation shock when a shock is advised;
a battery coupled to power circuitry of the AED;
a treatment protocol store which stores a treatment protocol by which the AED is controlled to deliver a single biphasic defibrillation shock in a first shock sequence followed by-multiple shocks in a second shock sequence, wherein the first shock sequence and the second shock sequence are always separated by a CPR period during which no defibrillation shock can be delivered; and
a controller coupled to the treatment protocol store which operates to execute the treatment protocol.

2. The AED of claim 1, wherein the multiple shocks of the second shock sequence are not separated by any CPR periods.

3. The AED of claim 2, wherein the treatment protocol further includes, after the CPR period separating the first shock sequence and the second shock sequence, analyzing the ECG signals using the ECG processor to determine whether a shock is advised, the first of the multiple shocks of the second shock sequence being delivered if the analyzing determines a shock is advised.

4. The AED of claim 3, wherein the treatment protocol further includes, after delivery of each of the multiple shocks of the second shock sequence, further analyzing the ECG signals using the ECG processor to determine whether a shock is advised, the next of the multiple shocks of the second shock sequence being delivered if the further analyzing determines a shock is advised.

5. The AED of claim 4 wherein the treatment protocol further includes a second CPR period after delivery of the last of the multiple shocks of the second shock sequence.

6. The automatic external defibrillator of claim 1, further including:
a user control, operable by an administrator to select the treatment protocol by means of software resident on the AED, without removal of the battery or connection of external hardware or software to the AED.

7. The automatic external defibrillator of claim 6, wherein the user control comprises a button on the AED.

8. The automatic external defibrillator of claim 7, wherein the button is operable to also control another function of the AED,
wherein operation of the button for selection of a treatment protocol is different from operation of the button to control the other function.

9. The automatic external defibrillator of claim 7, wherein the button further comprises a plurality of buttons.

10. The automatic external defibrillator of claim 6, further comprising a display located on the AED,
wherein the user control is operable with the display to select a protocol.

11. The automatic external defibrillator of claim 6, further comprising a loudspeaker which issues audible prompts,
wherein the user control is operable in conjunction with an audible prompt to select a protocol.

12. The automatic external defibrillator of claim 1, wherein the treatment protocol includes the single shock protocol for delivery of a biphasic shock of a given energy level and the multiple shock protocol for delivery of a sequence of shocks of at least two different energy levels.

13. The automatic external defibrillator of claim 12, wherein execution of the single shock protocol delivers a biphasic shock of at least 150 Joules.

14. The automatic external defibrillator of claim 12, wherein execution of the single shock protocol delivers a biphasic shock of at least 200 Joules.

15. The AED of claim 1, wherein the treatment protocol further includes, after the CPR period separating the first shock sequence and the second shock sequence, analyzing the ECG signals using the ECG processor to determine whether a shock is advised, the first of the multiple shocks of the second shock sequence being delivered if the analyzing determines a shock is advised.

* * * * *